(12) United States Patent
Mohr et al.

(10) Patent No.: US 6,329,558 B1
(45) Date of Patent: Dec. 11, 2001

(54) METHOD FOR PRODUCING ALKYLENE GLYCOL WITH A LOW CARBONYL COMPOUND CONTENT

(75) Inventors: Jürgen Mohr, Grünstadt; Toni Dockner, Meckenheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,229

(22) PCT Filed: Dec. 23, 1998

(86) PCT No.: PCT/EP98/08462

§ 371 Date: Jun. 23, 2000

§ 102(e) Date: Jun. 23, 2000

(87) PCT Pub. No.: WO99/33774

PCT Pub. Date: Jul. 8, 1999

(30) Foreign Application Priority Data

Dec. 23, 1997 (DE) .............................................. 197 57 711

(51) Int. Cl.$^7$ ............................ C07C 27/26; C07C 27/00
(52) U.S. Cl. ........................ 568/868; 568/858; 568/867; 568/914; 568/913
(58) Field of Search ................................... 568/913, 914, 568/858, 867, 868

(56) References Cited

U.S. PATENT DOCUMENTS

| 4,028,195 | * | 6/1977 | Becker et al. ........................ 203/38 |
| 4,937,393 | | 6/1990 | Masuda et al. . |
| 6,133,489 | * | 10/2000 | Mohr et al. ........................ 568/914 |

FOREIGN PATENT DOCUMENTS

| 0 226 799 | | 7/1987 | (EP) . |
| WO-9727164-A1 | * | 7/1997 | (WO) . |

* cited by examiner

Primary Examiner—Samuel Barts
Assistant Examiner—Elvis O. Price
(74) Attorney, Agent, or Firm—Oblon, Spivak, McClelland, Maier & Neustadt, P.C.

(57) ABSTRACT

In a process for isolating alkylene glycol having a low aldehyde content, in which a mixture comprising alkylene glycol is subjected to a final distillation, formic acid or a formate or a mixture of two or more formates or a mixture of formic acid and one or more formates is present in the mixture comprising alkylene glycol.

27 Claims, No Drawings

METHOD FOR PRODUCING ALKYLENE GLYCOL WITH A LOW CARBONYL COMPOUND CONTENT

This is the National Phase Application of PCT/EP98/08462, filed Dec. 23, 1998.

A The present invention relates to a process for isolating alkylene glycol having a low content of carbonyl compounds, in which a mixture comprising alkylene glycol is subjected to a final distillation, wherein formic acid or a formate or a mixture of two or more formates or a mixture of formic acid and one or more formates is present in the mixture comprising alkylene glycol.

Alkylene glycols, in particular ethylene glycol, have, since they were first synthesized by Wurtz (1859), developed into a major organic chemical product whose world production is millions of metric tons per year. A large part of the ethylene glycol is used for antifreezes, e.g. for automobiles, refrigeration plants, sprinkler facilities and the like. Owing to its low relative molar mass and its high boiling point, ethylene glycol is very well suited for antifreezes. Glycol is reacted on an industrial scale with polybasic carboxylic acids to produce polyesters which are employed as structural materials, raw materials for coatings, plasticizers and raw materials for fibers. Owing to their great importance as raw material for fibers, particular mention may be made, for example, of the polyester of ethylene glycol and terephthalic acid.

In cosmetics, ethylene glycol and diethylene glycol serve, for example, as solubilizers for water-insoluble substances and as humectants. Esterification of glycol with acetic acid gives the monoacetate and diacetate of ethylene glycol, both of which, like ethylene glycol itself, are employed as low-volatility solvents in the surface coatings industry.

The higher alkylene glycols are generally employed mainly in the area of polyester and polyurethane production, although the importance of such higher alkylene glycols remains far behind the economic importance of ethylene glycol.

Particularly when alkylene glycols, especially ethylene glycol, are to be used in the production of polyesters or polyurethanes, the purity of the alkylene glycols has to meet particular requirements. In general, even small traces of impurities are not tolerated by the processors.

The preparation of alkylene glycol can be carried out by numerous methods, for example by reaction of dichloroalkylene with alkali metal hydroxides or monochlorohydroxyalkylene with alkali metal hydroxides. However, such methods have no industrial importance. Industrially, alkylene glycols are produced virtually exclusively from alkylene oxides which are reacted with water in an exothermic reaction. The reaction of ethylene oxide with water is virtually complete in a few minutes at elevated temperature. Apart from increasing the reaction temperature, the reaction rate can also be influenced by acidic or basic catalysts.

In the above-described process which is known per se, the alkylene oxide, in particular ethylene oxide, is generally reacted with water in special reactors and under appropriate conditions and the resulting aqueous solution is then, in a plurality of stages, concentrated and the crude glycol is finally purified by fractionation, in general by fractional distillation.

Distillation processes and apparatuses for the purification of alkylene glycol are known in a wide variety of forms (cf., for example: Ullmanns Encyklopädie der technischen Chemie, 4$^{th}$ edition, VCH 1974, volume 8, p. 200 ff.). The purification is usually carried out using a number of columns connected in series, with firstly water, then the alkylene glycol and finally the corresponding, higher glycol ethers being obtained continuously.

A process for preparing ethylene glycol is described, for example, in EP-B 0 226 799. Here, ethylene oxide is reacted with water in the presence of a catalyst at from 30 to 300° C. for a defined time, under atmospheric or superatmospheric pressure. The catalyst used is, for example, a salt of a carboxylic acid, with salts of formic acid being mentioned among others. Before the resulting mixture comprising alkylene glycol is subjected to a final distillation, water and the catalyst are removed first.

Like all alcohols, alkylene glycols are readily oxidized both thermally (autooxidation) and catalytically; the products of such a reaction with oxygen, or other oxidants, are aldehydes (glycol aldehyde, glyoxal, formaldehyde, acetaldehyde) and the corresponding acids.

The technical-grade alkylene oxide used for preparing alkylene glycols also contains carbonyl compounds as a result of its production. However, the presence of such oxidation products is extremely undesirable, for example when the alkylene glycols are used for preparing polymers, and is generally limited strictly by detailed specifications laid down by the users.

Owing to the high boiling points of alkylene glycols, for example ethylene glycol, the purification of alkylene glycols by final distillation generally takes place under reduced pressure. Since virtually every distillation plant allows some slight amount of the surrounding atmosphere to enter the distillation plant, atmospheric oxygen also gets into the distillation plant during the distillation and can cause formation of the abovementioned oxidation products. Catalytic processes on the surfaces of the distillation plant may play an additional and reinforcing role. As a consequence, the alkylene glycol has a not negligible content of carbonyl compounds which can, firstly, originate from the alkylene oxides used for preparing the alkylene glycol, but can also be formed in the distillation plant during the purification by final distillation. In general, these carbonyl compounds have a boiling point lower than or similar to the alkylene glycols, so that the carbonyl compounds present as impurities do not remain in the distillation bottoms, but generally go over into the purified product. However, this is undesirable for the abovementioned reasons.

It is an object of the present invention to provide a process which makes it possible to purify mixtures comprising alkylene glycol in a final distillation so that a very small amount of carbonyl compounds is present in the purified alkylene glycol.

We have found that this object is achieved by formic acid or formates being present during the final distillation in the mixture comprising alkylene glycol which is to be distilled.

The present invention accordingly provides a process for isolating alkylene glycol having a low content of carbonyl compounds, in which a mixture comprising alkylene glycol is subjected to a final distillation, wherein formic acid or a formate or a mixture of two or more formates or a mixture of formic acid and one or more formates is present in the mixture comprising alkylene glycol during the final distillation.

The present invention thus provides a process which enables particularly pure alkylene glycol having a particularly low content of carbonyl compounds to be isolated. The process is accordingly one which concludes the synthesis of the alkylene glycol, and the alkylene glycol is subsequently in a form in which it can be passed on to the respective user, for example a polymer producer.

For the purposes of the present invention, a "final distillation" is a distillation in which the alkylene glycol is obtained in a ready-to-use state. The final distillation can be a last distillation of a preceding series of distillative purification steps, but can also be the only distillation carried out for isolating an alkylene glycol having a particularly low content of carbonyl compounds.

The number of distillation steps which precede the final distillation depends greatly on the mixture comprising alkylene glycol which is subjected to the process of the present invention.

Thus, for example, the process of the present invention can be employed for treating mixtures whose alkylene glycol content is 99% by weight or above. The important point here is that the distillation step of the present invention achieves a significant reduction in the content of carbonyl compounds.

It is also possible to use mixtures whose alkylene glycol content is, for example, in a range from about 60 to 99% by weight, as are customarily obtained when using alkylene glycols for drying industrial gases. Such a mixture then usually comprises, apart from the alkylene glycol, further constituents such as water, hydrocarbons and carbonyl compounds. In the case of such a mixture comprising alkylene glycol, a possibility is, for example, to remove water and hydrocarbons from the mixture in one or more initial process steps to give a mixture which consists largely of alkylene glycol, is largely free of water and has an alkylene glycol content of, for example, more than about 99% by weight. Such a mixture can then be subjected to the final distillation according to the present invention.

A further group of mixtures which can advantageously be subjected to the process of the present invention are the usually aqueous mixtures comprising alkylene glycol which are obtained in the preparation of alkylene glycols by hydrolysis of alkylene oxides. Such mixtures comprise, for example, from about 5 to 80% by weight of alkylene glycol plus, in general, residual amounts of ethylene oxide, higher alkylene glycol ethers, water, carbonyl compounds and possibly catalysts.

The mixture comprising alkylene glycol additionally contains formic acid or a formate or a mixture of two or more formates or a mixture of formic acid and one or more formates.

Suitable formates are essentially all formates, but particularly suitable formates are the alkali metal formates, for example the formates of lithium, sodium or potassium, or ammonium formates as are obtainable, for example, from formic acid and ammonia or organic amines. Particular preference is given to sodium formate and potassium formate.

The amount of formates present in the mixture comprising alkylene glycol during the final distillation can be chosen at will. Good results are achieved, for example, when the mixture comprising alkylene glycol contains, during the final distillation, at least an amount of formic acid or a formate or a mixture of two or more formates or a mixture of formic acid and one or more formates corresponding approximately to the stoichiometric content of carbonyl compounds. The amount of formates present in the mixture comprising alkylene glycol which is to be finally distilled can be determined prior to the final distillation by methods customary in chemical analysis, for example by means of gas chromatography.

If, for example, a content of carbonyl compounds of about 50 ppm is determined (based on the total mixture comprising alkylene glycol), then the content of formic acid or a formate or a mixture of two or more formates or a mixture of formic acid and one or more formates is advantageously at least about 50 ppm. At correspondingly higher contents of carbonyl compounds, for example about 100 ppm, 200 ppm, 300 ppm or above, it is advantageous to use at least about 100 ppm, 200 ppm, 300 ppm or more, respectively, of formic acid or a formate or a mixture of two or more formates or a mixture of formic acid and one or more formates.

In a preferred embodiment of the invention, the amount of formic acid or a formate or a mixture of two or more formates or a mixture of formic acid and one or more formates is, however, greater than the amount of carbonyl compounds in the mixture comprising alkylene glycol, for example about 0.1% by weight, about 0.2% by weight or about 0.5% by weight, or above, for example about 0.8% by weight, or about 1% by weight, in each case based on the total mixture comprising alkylene glycol.

In customary processes for preparing alkylene glycols by hydrolysis of alkylene oxides, preference is given to using alkylene oxides of the formula I

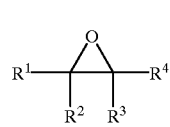

where $R^1$, $R^2$, $R^3$ and R4 are identical or different and are each, independently of one another, hydrogen, $C_{1-10}$-alkyl, $C_{2-10}$-alkenyl, $C_{2-10}$-alkynyl, $C_{3-10}$-cycloalkyl, $C_{3-10}$-cycloalkenyl, $C_{6-12}$-aryl or heteroaryl, where the alkyl, alkenyl or alkynyl radicals may be linear or branched and may in turn bear further functional groups, and the cycloalkyl, aryl and heteroaryl radicals may in turn bear further functional groups or may be substituted by $C_{1-10}$-alkyl, alkenyl, alkynyl or aryl radicals.

Preferred alkylene oxides are, for example, ethylene oxide, propylene oxide, butylene oxide, isobutylene oxide, 1,2-butylene oxide, 2,3-butylene oxide, pentylene oxide and styrene oxide, or mixtures of two or more thereof, with particular preference being given to ethylene oxide, propylene oxide or 1,2-butylene oxide, or mixtures of two or more thereof.

The alkylene oxides or mixtures of two or more different alkylene oxides which can usually be used in processes for preparing alkylene glycols can come from any source or from a variety of freely chosen sources, i.e. can have been prepared by any desired process. For example, ethylene oxide can be obtained by catalytic oxidation of ethylene in a process in which ethylene and a gas comprising molecular oxygen, for example air, oxygen-enriched air or pure oxygen, are reacted in the gas phase over a silver-containing catalyst.

The alkylene oxide which can usually be used in the preparation of alkylene glycol, or the mixture of two or more different alkylene oxides, is preferably used in pure form. This means that the alkylene oxide used or the alkylene oxides used are essentially free of impurities and thus contain essentially 100% of the alkylene oxide or the mixture of two or more different alkylene oxides. However, it is likewise possible, possibly with acceptance of lower yields or lower selectivity, or both, to use a technical grade of alkylene oxide which still contains impurities as are usually present prior to the purification of the alkylene oxide after its production.

Water customarily used in the preparation of alkylene glycols can originate from a wide variety of sources and does not have to meet any particular purity requirements. It is, for example, possible to use fresh water as is generally obtainable from process water treatment plants or, for example, from water companies, water which has been subjected to ion exchange, steam condensate and also usually water of reaction obtainable in chemical reactions which eliminate water.

In general, the preparation of alkylene glycols is carried out at a weight ratio of water to compounds bearing alkylene oxide groups of from about 1 to 20. The weight ratio of water to compounds bearing alkylene oxide groups is preferably greater than 1 and less than about 10, in particular less than about 7.6, and is particularly preferably from about 1.5 to about 4.5.

The process of the present invention for isolating alkylene glycol having a low content of carbonyl compounds can in principle be applied to a wide variety of mixtures comprising alkylene glycol, regardless of the source from which they originate. Thus, for example, it is possible to use mixtures comprising alkylene glycol which are obtained as product mixtures in the preparation of alkylene glycols by hydrolysis of alkylene oxides with or without the aid of various catalyst systems.

If alkylene glycols are prepared by aqueous hydrolysis of alkylene oxides without addition of catalysts, this is carried out, for example, under superatmospheric pressure and at elevated temperature.

If catalysts are used, they are, in particular, water-soluble inorganic or organic bases. The inorganic bases include, for example, the hydroxides, carbonates, hydrogencarbonates or oxides of the alkali metals and alkaline earth metals. In particular, they are the hydroxides, carbonates and hydrogencarbonates of lithium, sodium, potassium, rubidium, cesium, barium and calcium, with the hydroxides of sodium and potassium being particularly preferred.

Further catalysts which can be used are, for example, alkali metal formates or mixtures of two or more alkali metal formates. For the purposes of the present invention, the alkali metals in the alkali metal formates can be any alkali metals, i.e. lithium, sodium, potassium, rubidium or cesium, with preference usually being given to sodium and potassium.

It is likewise possible to use the hydroxides or oxides of the abovementioned alkali metals as catalysts.

Further catalysts which can be used are alkali metal carbonates or mixtures of two or more alkali metal carbonates or alkali metal bicarbonates or mixtures of two or more alkali metal bicarbonates, with the abovementioned alkali metals, in particular sodium and potassium, being used. It is also possible to use catalyst mixtures of the abovementioned alkali metal carbonates and alkali metal bicarbonates, in particular mixtures in which the proportion of alkali metal bicarbonates in the mixture predominates, i.e. is greater than 1. In particular, preference is given to mixtures in which the weight ratio of alkali metal bicarbonate to alkali metal carbonate is from about 1.1 to about 10.

The abovementioned catalysts are used individually or in admixture with one another. Thus, for example, when the catalyst used is a formate, it can be advantageous to add an alkali metal hydroxide to the formate to increase the pH to 8.1 or more, for example 9, 10 or 11.

The proportion by weight of the catalyst in such processes is usually, based on the total mass of water and alkylene oxide or the mixture of two or more different alkylene oxides, from about 1 to about 50% by weight. The proportion by weight of basic catalyst in the reaction mixture, based on the total mass of water and alkylene oxide or the mixture of two or more different alkylene oxides, is preferably more than about 2% by weight, particularly preferably more than about 5% by weight, for example about 6% by weight, 10% by weight, 15% by weight or 20% by weight, or above.

The reaction temperature in the preparation of the alkylene oxides is generally in the range from about 50 to about 250° C., preferably from about 80 to about 150° C., with preference being given to temperatures of, for example, 90° C., 100° C., 110° C. or 120° C. The reaction time can, for example as a function of the reaction temperature and the amount of basic catalyst used, be varied within a broad range. A lower limit for the reaction time is, for example, about 0.5 hour, but a lower limit of the reaction time of about 1 hour or 2 hours should generally be adhered to. The upper limit for the reaction time is, for example, about 10 hours for economic reasons, although this time may, if desired, be extended. Good results are achieved, for example, at reaction times of from about 3 hours to about 6 hours, in particular from about 4 hours to about 5 hours.

An addition of carbon dioxide can be made when carrying out the process of the present invention, but is generally not necessary. In a preferred embodiment of the invention, no external addition of carbon dioxide is employed. In a further preferred embodiment of the invention, carbon dioxide is largely excluded, i.e. the carbon dioxide content of the total reaction mixture is less than 0.1 mmol/mol of alkylene oxide groups, preferably less than 0.01 mmol/mol of alkylene oxide groups.

The reaction can be carried out isothermally, but it is also possible to carry out the reaction adiabatically in the process of the present invention. Here, the reaction temperature can have a ramp, with the reaction temperature being from about 80 to about 120° C. at the beginning and from about 160 to about 210° C. at the end of the reaction.

The pressure prevailing during the reaction can likewise be varied within wide limits. The reaction can be carried out at ambient pressure, i.e. generally about 1 bar, as long as the boiling points of the reactants present in the reaction mixture allow this. However, the reaction will generally be carried out under superatmospheric pressure, i.e. at a pressure of more than about 1 bar up to about 10 bar, for example about 2, about 4, about 6 or about 8 bar.

The process of the present invention is usually carried out either batchwise or continuously.

In a batch process, the reaction is carried out in a closed apparatus, and water and the basic catalyst are placed in the apparatus in any order and then, if desired after the water/catalyst mixture has been brought to the reaction temperature, the alkylene oxide or the mixture of two or more different alkylene oxides is added. The addition of gaseous alkylene oxides is generally carried out by means of an appropriate gas supply, so that the reaction mixture may be under pressure during the reaction. If liquid or solid alkylene oxides are to be reacted for the purposes of the present invention, they are generally added to the reaction mixture together with the water and the basic catalyst, with the order of addition being unimportant.

If the process of the present invention is carried out continuously, this is advantageously done in a tube reactor. Here too, the reaction can be carried out isothermally or isobarically or adiabatically.

The process of the present invention for isolating alkylene glycol having a low content of carbonyl compounds can be advantageously employed in conjunction with a process for preparing alkylene glycol.

The present invention therefore also provides a process for preparing alkylene glycol having a low content of carbonyl compounds, in which a reaction mixture comprising an alkylene oxide of the formula I

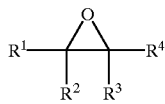

(I)

where $R^1$, $R^2$, $R^3$ and $R^4$ are identical or different and are each, independently of one another, hydrogen, $C_{1-10}$-alkyl, $C_{2-10}$-alkenyl, $C_{2-10}$-alkynyl, $C_{3-10}$-cycloalkyl, $C_{3-10}$-cycloalkenyl, $C_{6-12}$-aryl or heteroaryl, where the alkyl, alkenyl or alkynyl radicals may be linear or branched and may in turn bear further functional groups, and the cycloalkyl, aryl and heteroaryl radicals may in turn bear further functional groups or may be substituted by $C_{1-10}$-alkyl, alkenyl, alkynyl or aryl radicals, or a mixture of two or more thereof, and also water and, if desired, a catalyst is reacted to form a product mixture comprising alkylene glycol which is subsequently subjected to a final distillation, wherein formic acid or a formate or a mixture of two or more formates or a mixture of formic acid and one or more formates is present in the product mixture during the final distillation for isolating an alkylene glycol having a low content of carbonyl compounds.

The process of the present invention for preparing an alkylene glycol having a low content of carbonyl compounds can be carried out in the absence of a catalyst, but it is advantageous to use one of the abovementioned catalysts. The presence of a basic catalyst in the reaction mixture is particularly preferred. In a preferred embodiment, the reaction mixture comprises, as basic catalyst, at least one compound selected from the group consisting of alkali metal hydroxides, alkali metal carbonates, alkali metal hydrogencarbonates, alkali metal formates, ammonium formates, tertiary amines or a mixture of two or more thereof.

Advantageous results are obtained, for example, when the preparation of the alkylene glycol is carried out using a catalyst which comprises at least a proportion of formic acid or a formate or a mixture of two or more formates or a mixture of formic acid and one or more formates.

The final distillation is preferably carried out at a pressure of less than 500 mbar, particularly preferably a pressure of less than 200 mbar. For example, the pressure can be 100 mbar, 50 mbar or less, for example 30 mbar, 20 mbar or less.

Depending on the boiling point of the alkylene glycol or the individual alkylene glycols to be separated in a mixture of two or more different alkylene glycols, it is possible, for example, to work at different bottom temperatures which are naturally related to the prevailing pressure in each case. Advantageous results can be achieved when, for example, a bottom temperature of at least about 120° C. is employed. If, for example, a lower alkylene glycol having up to 4 carbon atoms is finally distilled, it is advantageous to employ a bottom temperature of from about 140 to about 160° C. and a pressure of from about 120 to about 210 mbar.

In its most general form, the present invention provides for the use of formic acid or a formate or a mixture of two or more formates or a mixture of formic acid and one or more formates for suppressing the formation of carbonyl compounds in processes for isolating or preparing alkylene glycol having a low content of carbonyl compounds, and also to the use of formic acid or a formate or a mixture of two or more formates or a mixture of formic acid and one or more formates for suppressing the formation of carbonyl compounds during the purification of mixtures comprising alkylene glycol by distillation.

The invention is illustrated by the examples below, without being restricted thereby.

EXAMPLES

Distillation of Ethylene Glycol

In a simple distillation apparatus comprising a distillation pot, a Claisen attachment and a descending condenser with vacuum connection, ethylene glycol was distilled at a bottom temperature of about 150° C. and a temperature at the top of about 140° C. under a reduced pressure of from 160 to 170 mbar, with about 5% of the initial material remaining as residual bottoms at the end.

The distillation was carried out with and without addition according to the present invention of formic acid salts to the glycol to be distilled; the aldehyde content before and after the distillation was determined by analysis using the known method of oxime titration, which gives the total content of aldehyde (free and bound as acetal).

Results

The glycol used had an aldehyde content (calculated as acetaldehyde) of 55 ppm. After distillation without additive, the aldehyde content in the distillate was unchanged compared to the initial material.

An addition of 0.5% by weight of potassium formate to the initial material gave a distillate containing 16 ppm of total aldehyde; 0.5% of ammonium formate gave 11 ppm.

We claim:

1. A process for isolating alkylene glycol having a reduced content of carbonyl compounds therein, which comprises subjecting alkylene glycol to a final distillation, wherein formic acid or a formate, or a mixture of two or more formates, or a mixture of formic acid and one or more formates selected from the group consisting of lithium formate, sodium formate, potassium formate and ammonium formate, is present in a mixture comprising alkylene glycol during the final distillation.

2. The process of claim 1, wherein the mixture comprising alkylene glycol has a water content of less than 200 ppm.

3. The process of claim 1, wherein the mixture comprising alkylene glycol comprises at least an amount of a formate or a mixture of two or more formates or a mixture of formic acid and one or more formates corresponding to a stoichiometric content of carbonyl compounds.

4. The process of claim 1, wherein the final distillation is effected at a pressure of less than 500 mbar.

5. The process of claim 1, wherein the final distillation is effected at a bottom temperature of at least 120° C.

6. The process of claim 1, wherein said alkylene glycol subjected to said final distillation comprises a mixture having an alkylene glycol content of 99% by weight or above.

7. The process of claim 1, wherein the final distillation is effected at a pressure of less than 200 mbar.

8. The process of claim 7, wherein the final distillation is effected at a pressure of less than 100 mbar.

9. The process of claim 8, wherein the final distillation is effected at a pressure of less than 50 mbar.

10. The process of claim 1, wherein the final distillation is effected at a bottom temperature of from about 140 to about 160° C. and a pressure of from about 120 to about 210 mbar.

11. The process of claim 1, wherein the amount of said formate, or said mixture of two or more formates, or said mixture of formic acid and one or more formates is used in an amount greater than that of the carbonyl compounds in the mixture.

12. The process of claim 11, wherein the amount of said formate, or said mixture of two or more formnates, or said mixture of formic acid and one or more formates is used in an amount of about 0.1% by weight to about 0.5% by weight greater than that of the carbonyl compounds in the mixture.

13. The process of claim 1, wherein a formate, or a mixture of two or more formates, or a mixture of formic acid and one or more formates is present in the mixture comprising alkylene glycol during the final distillation.

14. The process of claim 13, wherein a formate is present in the mixture comprising alkylene glycol during the final distillation.

15. The process of claim 14, wherein the formate is potassium formate or ammonium formate.

16. The process of claim 1, wherein the carbonyl compounds comprise aldehydes.

17. The process of claim 1, wherein said reduced content of carbonyl compounds in said alkylene glycol comprises 16 ppm or less thereof.

18. A process for preparing alkylene glycol having a reduced content of carbonyl compounds therein, which comprises:

a) reacting one or more alkylene oxides having the formula (I) with water, optionally in the presence of a catalyst to form a product mixture comprising alkylene glycol;

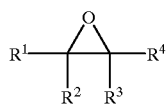

(I)

wherein:

$R_1$, $R_2$, $R_3$ and $R_4$ are each identical or different and are each, independently of one another, hydrogen $C_1$–$C_{10}$-alkyl, $C_2$–$C_{10}$-alkenyl, $C_2$–$C_{10}$-alkynyl, $C_3$–$C_{10}$-cycloalkyl, $C_3$–$C_{10}$-cycloalkenyl, $C_6$–$C_{12}$-aryl or heteroaryl, wherein the alkyl, alkenyl or alkynyl groups are linear or branched and optionally contain functional groups, and wherein the cycloalkyl, aryl and heteroaryl groups optionally contain functional groups or are optionally substituted by $C_1$–$C_{10}$-alkyl, alkenyl, alkynyl or aryl; and b) subjecting the product mixture to a final distillation, wherein formic acid or a formate, or a mixture of two or more formates, or a mixture of formic acid and one or more formates selected from the group consisting of lithium formate, sodium formate, potassium formate an ammonium formate, is present in a mixture comprising alkylene glycol during the final distillation.

19. The process of claim 18 wherein the reaction mixture in step a) comprises a catalyst, which is a basic catalyst.

20. The process of claim 19, wherein said basic catalyst is at least one compound selected from the group consisting of alkali metal hydroxides, alkali metal carbonates, alkali metal hydrogen carbonates, alkali metal formates, ammonium formates, tertiary amines or mixtures of two or more thereof which are present in the reaction mixture.

21. The process of claim 18, wherein the amount of said formate, or said mixture of two or more formates, or said mixture of formic acid and one or more formates is used in an amount greater than that of the carbonyl compounds in the mixture.

22. The process of claim 21, wherein the amount of said formate, or said mixture of two or more formates, or said mixture of formic acid and one or more formates is used in an amount of about 0.1% by weight to about 0.5% by weight greater than that of the carbonyl compounds in the mixture.

23. A The process of claim 18, wherein a formate, or a mixture of two or more formates, or a mixture of formic acid and one or more formates is present in the mixture comprising alkylene glycol during the final distillation.

24. The process of claim 23, wherein a formate is present in the mixture comprising alkylene glycol during the final distillation.

25. The process of claim 24, wherein the formate is potassium formate or ammonium formate.

26. The process of claim 18, wherein the carbonyl compounds comprise aldehydes.

27. The process of claim 18, wherein said reduced content of carbonyl compounds in said alkylene glycol comprises 16 ppm or less.

* * * * *

UNITED STATES PATENT AND TRADEMARK OFFICE
CERTIFICATE OF CORRECTION

PATENT NO. : 6,329,558 B1
DATED : December 11, 2001
INVENTOR(S) : Juergen Mohr et al.

It is certified that error appears in the above-identified patent and that said Letters Patent is hereby corrected as shown below:

Column 1,
Line 7, "A The present invention" should read -- The present invention --.

Column 8,
Line 38, "formic acid or a formate" should read -- a formate --.

Column 9,
Line 7, "formnates, or said" should read -- formates, or said --.

Column 10,
Line 6, "formic acid or a formate" should read -- a formate --.

Signed and Sealed this

Tenth Day of September, 2002

Attest:

Attesting Officer

JAMES E. ROGAN
*Director of the United States Patent and Trademark Office*